US008980870B2

(12) United States Patent
Nakatani et al.

(10) Patent No.: US 8,980,870 B2
(45) Date of Patent: *Mar. 17, 2015

(54) SOLID TELMISARTAN PHARMACEUTICAL FORMULATIONS

(75) Inventors: Manabu Nakatani, Kawanishi (JP); Sawada Takeshi, Ikeda (JP); Toshimitsu Ohki, Ikeda (JP); Kenzo Toyoshima, Ikoma (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 291 days.

This patent is subject to a terminal disclaimer.

(21) Appl. No.: 10/664,725

(22) Filed: Sep. 18, 2003

(65) Prior Publication Data

US 2004/0110813 A1    Jun. 10, 2004

Related U.S. Application Data

(60) Provisional application No. 60/415,357, filed on Oct. 2, 2002.

(30) Foreign Application Priority Data

Sep. 24, 2002  (DE) ................................ 102 44 681

(51) Int. Cl.
| | |
|---|---|
| A01N 43/00 | (2006.01) |
| A61K 31/33 | (2006.01) |
| A61K 9/20 | (2006.01) |
| A61K 9/24 | (2006.01) |
| A61K 9/48 | (2006.01) |
| A61K 9/16 | (2006.01) |
| A61K 31/4184 | (2006.01) |

(52) U.S. Cl.
CPC ............ *A61K 9/1641* (2013.01); *A61K 9/1623* (2013.01); *A61K 31/4184* (2013.01); *A61K 9/2018* (2013.01); *A61K 9/2031* (2013.01); *A61K 9/209* (2013.01)
USPC ............ 514/183; 424/451; 424/464; 424/472

(58) Field of Classification Search
None
See application file for complete search history.

(56) References Cited

U.S. PATENT DOCUMENTS

| | | | | | |
|---|---|---|---|---|---|
| 3,134,823 | A | * | 5/1964 | Brown | 585/310 |
| 3,879,408 | A | * | 4/1975 | Sellstedt | 540/304 |
| 4,522,818 | A | * | 6/1985 | Raghunathan | 514/155 |
| 5,232,706 | A | * | 8/1993 | Palomo Coll | 424/475 |
| 5,547,603 | A | | 8/1996 | Sörensson | |
| 5,547,683 | A | | 8/1996 | Yano et al. | |
| 5,697,922 | A | | 12/1997 | Thombre | |
| 5,994,348 | A | | 11/1999 | Ku et al. | |
| 6,068,859 | A | * | 5/2000 | Curatolo et al. | 424/490 |
| 6,071,939 | A | | 6/2000 | Gaviraghi | |
| 6,162,615 | A | * | 12/2000 | Zielenski | 435/26 |
| 6,248,729 | B1 | | 6/2001 | Coniglio et al. | |
| 6,270,745 | B1 | * | 8/2001 | Duatti et al. | 424/1.77 |
| 6,342,247 | B1 | | 1/2002 | Ku et al. | |
| 6,358,986 | B1 | * | 3/2002 | Schneider | 514/394 |
| 6,383,471 | B1 | | 5/2002 | Chen | |
| 6,395,300 | B1 | * | 5/2002 | Straub et al. | 424/489 |
| 2002/0019431 | A1 | * | 2/2002 | Straub et al. | 514/406 |
| 2002/0137678 | A1 | * | 9/2002 | Gendron et al. | 514/12 |
| 2003/0220297 | A1 | * | 11/2003 | Berstein et al. | 514/80 |
| 2004/0058914 | A1 | * | 3/2004 | Doi et al. | 514/220 |
| 2004/0180085 | A1 | * | 9/2004 | Ohkouchi et al. | 424/465 |
| 2004/0198645 | A1 | * | 10/2004 | Ambuhl et al. | 514/11 |
| 2005/0089575 | A1 | * | 4/2005 | Friedl et al. | 424/474 |

FOREIGN PATENT DOCUMENTS

| | | | |
|---|---|---|---|
| AU | 9210707 A | * | 8/1992 |
| CA | 2472392 A1 | | 7/2003 |
| EP | 0747050 A1 | | 12/1996 |
| EP | 1197223 A1 | | 4/2002 |
| ES | 2124794 T3 | | 2/1999 |
| FR | 2 787 330 | | 6/2000 |
| FR | 2787330 A1 | | 6/2000 |
| WO | WO 99/17744 | * | 4/1999 |
| WO | 9947123 A1 | | 9/1999 |
| WO | WO 00/27397 | | 5/2000 |
| WO | 0059475 A1 | | 10/2000 |
| WO | 0072827 A2 | | 12/2000 |

(Continued)

OTHER PUBLICATIONS

Ethanol. Crystal Reference Encyclopedia (2001). Retrieved Nov. 10, 2005, from xreferplus. http://www.xreferplus.com/entry/931538.*
Profile of the Pharmaceutical Manufacturing Industry, Sep. 1997, p. 41.*
Parikh, DM Handbook of Pharmaceutical Granulation Technology, 1997, p. 92 and 244.*
Gennaro, A ed. Remington: The Science and Practice of Pharmacy vol. II, Mack Publishing Company:Easton 1995.*
Wienen et al. Cardiovascular Drug Reviews 2000 18:127-154.*
Micardis Reference 1998.*
Reynolds, ed., Martindale The Extra Pharmacopoeia, 29th ed., The Pharmaceutical Press London, England: 1989, p. XXVI.*
Patent Abstract—JP 2001-139461, Konishi, Ko, et al; Quickly Collapsable Tablet.
Patent Abstract—JP 2001-278812, Fukami, Jninchi, et al; Disintegrant for Tablet and Tablet using the same.

(Continued)

*Primary Examiner* — Juliet Switzer
*Assistant Examiner* — Caralynne Helm
(74) *Attorney, Agent, or Firm* — Michael P. Morris; Timothy X. Witkowski; Usha R. Patel

(57) ABSTRACT

A pharmaceutical composition comprising 3 wt. % to 50 wt. % telmisartan dispersed in a dissolving matrix comprising:
 (a) a basic agent in a molar ratio of basic agent:telmisartan of 1:1 to 10:|1|;
 (b) about 1 wt. % to about 20 wt. % of a surfactant or emulsifier;
 (c) 25 wt. % to 70 wt. % of a water-soluble |diluent|; and
 (d) 0 wt. % to 20 wt. % of one or more additional excipients and/or |adjuvants|;
wherein the sum of all components is 100%, methods of making such pharmaceutical compositions, and their use.

10 Claims, 1 Drawing Sheet

(56) References Cited

FOREIGN PATENT DOCUMENTS

WO     WO 01/37808     5/2001
WO     WO 03/059327 A1     7/2003

OTHER PUBLICATIONS

Disclosure of Prior Art Sate Under §102(b). (1 page) Jul. 18, 2011.
Lacourcière, Y., et al. "Comparison of the Antihypertensive Effects of a Fixed Dose Combination of Telmisartan and Hydrochlorothiazide Versus Telmisartan Monotherapy in Mild to Moderate Hypertensive Patients" The Canadian Journal of Cardiology, vol. 16 Supplement F, Scientific Program and Abstracts and 53$^{rd}$ Annual Meeting of the Canadian Cardiovascular Society (3 pages). (Sep. 2000).

McGill, J.B. et al. "Telmisartan Plus Hydrochlorothiazide Versus Telmisartan or Hydrochlorothiazide Monotherapy in Patients with Mild to Moderate Hypertension: A Multicenter, Randomized, Double-Blind, Placebo-Controlled, Parallel-Group Trial" Clinical Therapeutics, 23(6):833-850. (2001).
Passerini, Nadia et al. "Preparation and characterisation of ibuprofen-poloxamer 188 granules obtained by melt granulation" European Journal of Pharmaceutical Sceinces (2002) vol. 15, pp. 71-78.
Pieber, Doris et al. "Pressor and mesenteric arterial hyporesponsiveness to angiotensin II is an early event in haemorrhagic hypotension in anaesthetised rats" Cardiovascular Research (1999) vol. 44, pp. 166-175.
International Search Report for PCT/EP2003/010382 mailed Jan. 19, 2004. International Publication Number: WO2004/028505.

* cited by examiner

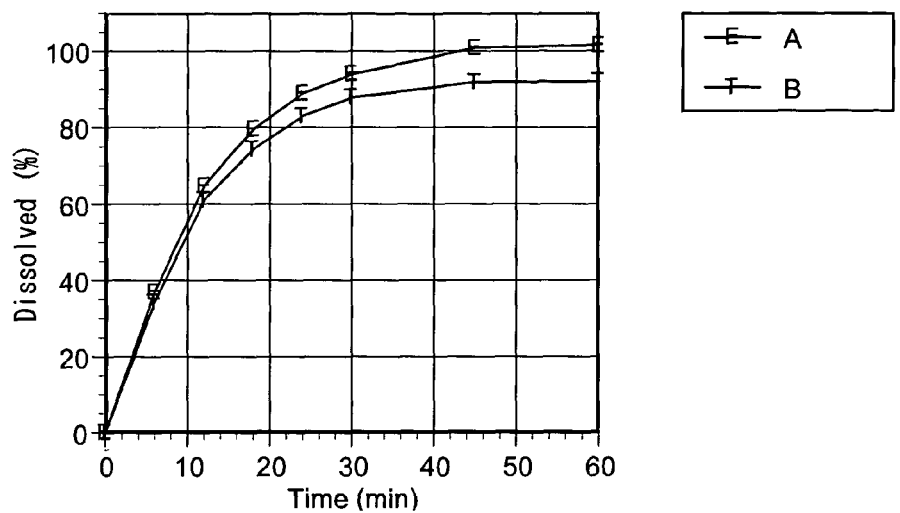
Figure 1: Dissolution of Capsule Formulations A and B in Aqueous Solution at pH 1.2
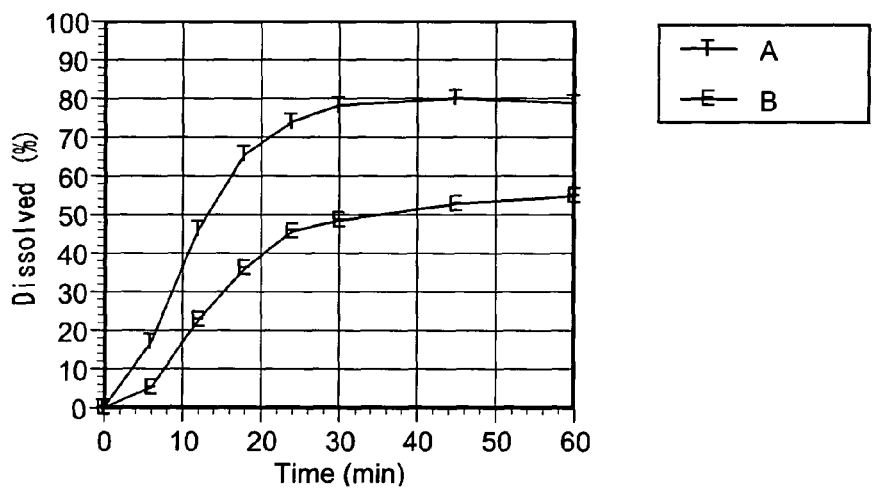
Figure 2: Dissolution of Capsule Formulations A and B in Aqueous Solution at pH 4.0

SOLID TELMISARTAN PHARMACEUTICAL FORMULATIONS

RELATED APPLICATIONS

This application claims priority to U.S. Ser. No. 60/415,357, filed Oct. 2, 2002, and German Application No. DE 102 44 681.4, filed Sep. 24, 2002, each of which is hereby incorporated by reference in its entirety.

FIELD OF THE INVENTION

The present invention relates to new solid pharmaceutical compositions comprising the angiotensin II receptor antagonist telmisartan, e.g., in form of granules or in form of a powder, as well as solid oral formulations ready for use/ingestion, e.g., capsule and tablet formulations made from said pharmaceutical compositions. The present invention also provides methods for producing such compositions and |formulations|.

BACKGROUND OF THE INVENTION

Telmisartan (INN) is an angiotensin II receptor antagonist developed for the treatment of hypertension and other medical indications as disclosed in EP 502 314 A (corresponding to U.S. Pat. No. 5,591,762). Telmisartan's chemical name is 4'-[2-n-propyl-4-methyl-6-(1-methylbenzimidazol-2-yl)benzimidazol-1-ylmethyl]biphenyl-2-carboxylic acid and has the following structure:

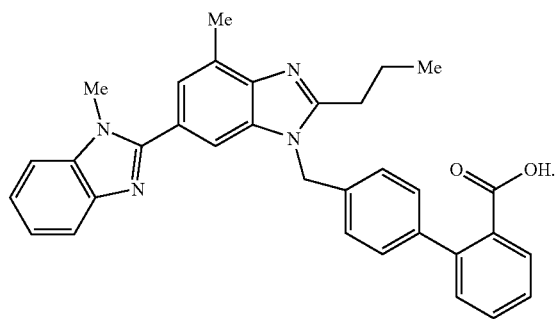 [SMILES: CCCc1nc2c(C)cc(-c3nc4ccccc4n3C)cc2n1Cc1ccc(-c2ccccc2C(=O)O)cc1]

Telmisartan is generally manufactured and supplied in the free acid form. As disclosed in WO 00/43370 (corresponding to U.S. Pat. Nos. 6,358,986 and 6,410,742), each of which is hereby incorporated by reference, crystalline telmisartan exists in two polymorphic forms having different melting points. Under the influence of heat and humidity, the lower melting polymorph B transforms irreversibly into the higher melting polymorph A. Both forms are characterized by a very poor solubility in aqueous |systems| at the physiological pH range of the gastrointestinal tract of between pH 1 to 7.

Telmisartan is obtainable on the market under the trademark MICARDIS®. Starting from the free acid form, telmisartan as introduced to the market is manufactured using an expensive spray-drying process. Due to the poor solubility of the free acid form, preparation of alternative telmisartan formulation is difficult.

SUMMARY OF THE INVENTION

There is a clear need to provide alternative solid oral formulations of telmisartan which can be prepared using less complicated and expensive processes and fulfill all prerequisites for pharmaceutical use, i.e., long-lasting stability of the formulation under different climatic conditions and sufficient solubility of the active substance for sufficient gastrointestinal absorption in the slightly acidic and neutral pH region.

It is a first object of the invention to provide such alternative solid pharmaceutical compositions comprising telmisartan, e.g., in form of granules or a powder, in a form allowing that the active compound is released with sufficient solubility for gastrointestinal absorption in the slightly acidic and neutral pH region from such compositions and formulations.

Preferably, the formulations should have immediate release characteristics and a dissolution showing no essential pH dependency within the physiological relevant pH interval of the gastrointestinal tract|.

It is a second object of the invention to provide further solid oral formulations ready for use/ingestion, e.g., capsule and tablet formulations, made from such pharmaceutical compositions mentioned under the first aspect of the invention.

A third object of the invention relates to methods for producing such compositions and |formulations| mentioned hereinbefore.

DESCRIPTION OF THE DRAWINGS

FIG. 1 shows the release profile of the active ingredient telmisartan from capsule Formulation A according to the invention in comparison to a corresponding capsule Formulation B without the poloxamer 188 component in aqueous test solution (JP $1^{st}$ fluid) at pH 1.2; and FIG. 2 shows the release profile of telmisartan from Formulation A in comparison to Formulation B in aqueous acetic-acid buffer at pH 4.0.

DETAILED DESCRIPTION OF THE INVENTION

First Object of the Invention (Pharmaceutical Composition)

Surprisingly it has been found that the solubility of telmisartan can be raised by a factor of several hundreds by a pharmaceutical composition comprising 3 wt. % to 50 wt. % |of| telmisartan dispersed in a dissolving matrix comprising:
  (a) a basic agent in a molar ratio of basic agent:telmisartan of 1:1 to 10:|1|;
  (b) a surfactant or emulsifier in an amount of about 1 wt. % to 20 wt. % of the final |composition|;
  (c) 25 wt. % to 70 wt. % of a water-soluble |diluent|; and
  (d) optionally 0 wt. % to 20 wt. % of further excipients and/or |adjuvants|,
the sum of all components adding to 100%.

The term "dissolving tablet matrix" refers to a pharmaceutical tablet base formulation having immediate release (fast dissolution) characteristics that readily dissolves in a physiological aqueous medium.

Specific examples of suitable basic agents are alkali metal hydroxides such as NaOH and KOH; furthermore $NaHCO_3$, $KHCO_3$, $Na_2CO_3$, $K_2CO_3$, $Na_2HPO_4$, $K_2HPO_4$, basic amino acids such as arginine, and meglumine (N-methyl-D-glucamine).

The surfactants and emulsifiers may be ionic or nonionic, the latter being preferred. Specific examples of surfactants and emulsifiers are such as poloxamers or pluronics, polyethylene glycols, polyethylene glycol monostearate, polysorbates, sodium lauryl sulfate, polyethoxylated and hydrogenated castor oil, etc.

With regard to the poloxamers or pluronics suitable as nonionic surfactants and emulsifiers, reference is made to the definition given in *The Merck Index*, 12$^{th}$ edition, (1996), which is herewith incorporated by reference. Suitable poloxamers may have an average molecular weight of about 2000 to 12000, preferably 4000 to 10000, more preferably 6000 to 10000, and most preferably 8000 to 9000. Examples for specific poloxamers are poloxamer 182LF, poloxamer 331, and poloxamer |188|.

Specific examples of suitable water-soluble diluents are carbohydrates such as monosaccharides such as glucose; oligosaccharides such as sucrose; and sugar alcohols such as erythritol, sorbitol, mannitol, dulcitol, ribitol, and xylitol. Mannitol, erythritol, sorbitol, and sucrose are preferred diluents.

The other excipients and/or adjuvants are, for instance, selected from binders, carriers, lubricants, flow control agents, crystallization retarders, solubilizers, and coloring agents.

The binder may be selected from the group of dry binders and/or the group of wet granulation binders, depending on the manufacturing process chosen for the pharmaceutical composition. Suitable dry binders are, e.g., cellulose powder, crystalline cellulose, microcrystalline cellulose, or light anhydrous silicic acid. Specific examples of wet granulation binders are corn starch, polyvinyl pyrrolidone (povidone), vinylpyrrolidone-vinylacetate copolymer (copovidone), and cellulose derivatives such as hydroxymethylcellulose, hydroxyethylcellulose, hydroxypropylcellulose, and hydroxypropylmethylcellulose.

Suitable disintegrants are, e.g., sodium starch glycolate, crospovidone, croscarmellose, sodium carboxymethylcellulose, and dried corn starch.

The other excipients and adjuvants, if used, are preferably selected from diluents and carriers such as cellulose powder, crystalline cellulose, or microcrystalline cellulose, cellulose derivatives such as hydroxymethylcellulose, hydroxyethylcellulose, hydroxypropylcellulose, and hydroxypropylmethylcellulose, dibasic calcium phosphate, corn starch, pregelatinized starch, polyvinyl pyrrolidone (povidone), etc.; lubricants such as stearic acid, magnesium stearate, sodium stearylfumarate, glycerol tribehenate, etc.; flow control agents such as colloidal silica, light anhydrous silicic acid, crystalline cellulose, talc, etc.; crystallization retarders such as povidone, etc.; coloring agents, including dyes and pigments such as Iron Oxide Red or Yellow, titanium dioxide, talc, etc.; and mixtures of two or more of these excipients and/or adjuvants.

The pharmaceutical compositions according to the present invention provide improved solubilization of the poorly water-soluble telmisartan of up to a concentration of more than 4.4 mg/100 mL, thereby facilitating dissolution of the drug at a physiological pH level, and also provides for immediate release from the fast disintegrating matrix.

The presence of component (b), a surfactant or emulsifier, is essential to achieve a substantially improved dissolution of the active ingredient as well as for the use of a simplified manufacture process such as fluid-bed granulation instead of spray-drying for preparing the solid pharmaceutical compositions according to the invention.

In a preferred embodiment the pharmaceutical composition according to the invention comprises 10 to 35 wt. % |of| telmisartan dispersed in a dissolving matrix comprising
(a) a basic agent, in a molar ratio of basic agent:telmisartan of 1.5:1 to 5:1|;
(b) a nonionic surfactant or emulsifier, in an amount of about 1 wt. % to 10 wt. % of the final |composition|;
(c) 35 wt. % to 60 wt. % of a water-soluble |diluent|; and
(d) optionally 0 wt. % to 20 wt. % of further excipients and/or |adjuvants|,
the sum of all components adding to 100%.

All specified components (a) to (d) mentioned hereinbefore may be used in the preferred embodiment, whereas:
preferred basic agents are NaOH, KOH, arginine, and meglumine,
preferred nonionic surfactants or emulsifiers are selected from poloxamers, polyethylene glycols, polyethoxylated, and hydrogenated castor oil,
preferred water-soluble diluents are selected from sucrose, erythritol, sorbitol, mannitol, and xylitol, and
preferred optional further excipients and/or adjuvants are selected from crystalline cellulose, light anhydrous silicic acid, hydroxymethylcellulose, hydroxyethylcellulose, hydroxypropylcellulose, hydroxypropylmethylcellulose, magnesium stearate, corn starch, polyvinyl pyrrolidone, vinylpyrrolidone-vinylacetate copolymer, stearic acid, magnesium stearate, sodium stearylfumarate, colloidal silica, talc, povidone, and coloring agents.

In a more preferred embodiment, the pharmaceutical composition according to the invention comprises 15 wt. % to 25 wt. % |of| telmisartan dispersed in a dissolving matrix comprising:
(a) a basic agent, in a molar ratio of basic agent:telmisartan of 2:1 to 3:1|;
(b) a nonionic surfactant or emulsifier, in an amount of about 2 wt. % to 7 wt. % of the final |composition|;
(c) 35 wt. % to 50 wt. % of a water-soluble ..diluent|; and
(d) optionally 0 wt. % to 20 wt. % of further excipients and/or |adjuvants|,
the sum of all components adding to 100%.

All specified components (a) to (d) mentioned hereinbefore may be used in the more preferred embodiment, whereas:
the most preferred basic agent is meglumine,
the most preferred nonionic surfactants are selected from poloxamers,
the most preferred water-soluble diluents are selected from mannitol, erythritol, sorbitol, and sucrose, and
the most preferred optional further excipients and/or adjuvants are selected from crystalline cellulose, light anhydrous silicic acid, and magnesium stearate.

In any embodiment of the invention, one or more of the nonionic surfactants or emulsifiers, water-soluble diluents and excipients and/or adjuvants may be present.

Second Object of the Invention (Formulation Ready for Use/Ingestion)

A second object of the invention is directed to solid oral formulations ready for use/ingestion, e.g., capsule and tablet formulations made from the pharmaceutical compositions mentioned hereinbefore. Capsule formulations can be obtained by simply filling the powdery or granulated pharmaceutical formulations mentioned hereinbefore in conventional capsules, for instance, hard or soft gelatine capsules. Tablet formulations also can be prepared by conventional techniques, for instance, by direct compression of the powdery or granular pharmaceutical compositions mentioned hereinbefore.

The tablets so obtained can be further processed using conventional techniques, for instance, they can be coated using suitable coatings known in the art which do not negatively affect the dissolution properties of the final formulation. For instance, the tablets can be provided with a seal coat for moisture protection by melting a high molecular weight polyethylene glycol or any polyethylene glycol which is solid at room temperature (25° C.) onto the core tablets. Even though the polymer is water soluble, its rate of solution is slow enough to afford the core tablets moisture protection. Other polymers, which offer similar water solubility and a similar degree of moisture protection may also be used.

Additionally, agents such as beeswax, shellac, cellulose acetate phthalate, polyvinyl acetate phthalate, zein, film forming polymers such as hydroxypropyl cellulose, ethylcellulose, and polymeric methacrylates can be dissolved in a suitable solvent and applied to the tablets, provided that the coating has no substantial effect on the disintegration/dissolution of the dosage form and that the coated dosage form is physiochemically stable.

After the dosage form is sealed, a sugar coating may be applied onto the sealed pharmaceutical dosage form. The sugar coating may comprise sucrose, dextrose, sorbitol, and the like or mixtures thereof. If desired, colorants or opacifiers may be added to the sugar solution.

Composition of both capsule and (core) tablet formulations, is preferably the same as mentioned hereinbefore with respect to the pharmaceutical formulations. In the alternative, additional amounts of the optional excipients and/or adjuvants mentioned hereinbefore can be added before filling the powdery or granulated pharmaceutical formulations into capsules or compressing them to tablets, e.g., in order to adjust the concentration of the active compound to a certain value (for instance, by adding more filler), to improve flowability of powdery formulations, to improve compressibility (for instance, by adding more lubricant or binder), or other routine process optimization known to the skilled person.

The solid oral formulations according to the present invention generally contain 10 mg to 160 mg, preferably 20 mg to 80 mg, of telmisartan. Presently preferred forms comprise 20 mg, 40 mg, or 80 mg of telmisartan, respectively.

For instance, the total composition of capsule and tablet formulations according to the invention may vary within the following ranges, with the proviso that the proportional composition given above with respect to the basic pharmaceutical compositions is met:

10 mg to 160 mg of |telmisartan|;
10 mg to 160 mg of |meglumine| or arginine, or 2 mg to 33 mg of |NaOH|, or 3 mg to 46 mg of |KOH|, or 4 mg to 80 mg of |NaHCO$_3$|, |KHCO$_3$|, |Na$_2$CO$_3$|, |K$_2$CO$_3$|, |Na$_2$HPO$_4$|, or |K$_2$HPO$_4$|;
2 mg to 40 mg of nonionic surfactants or emulsifiers;
20 mg to 200 mg of water soluble diluents; and
0 mg to 80 mg of further excipients and/or adjuvants, preferably:
20 mg to 80 mg of telmisartan;
20 mg to 80 mg of meglumine, or 4 mg to 16 mg of NaOH, or 6 mg to 23 mg of KOH;
4 mg to 20 mg of nonionic surfactants or emulsifiers selected from poloxamers, polyethylene glycols, or polyethoxylated and hydrogenated castor oil, poloxamers being especially preferred;
40 mg to 100 mg of water soluble diluents selected from glucose, sucrose, erythritol, sorbitol, mannitol, and xylitol; and
0.2 mg to 40 mg of further excipients and/or adjuvants selected from crystalline cellulose, light anhydrous silicic acid, hydroxymethylcellulose, hydroxyethylcellulose, hydroxypropylcellulose, hydroxypropylmethylcellulose, magnesium stearate, corn starch, polyvinyl pyrrolidone, vinylpyrrolidone-vinylacetate copolymer, stearic acid, magnesium stearate, sodium stearylfumarate, colloidal silica, talc, povidone, and coloring agents;

most preferred:
35 mg to 45 mg of telmisartan;
35 mg to 45 mg of meglumine;
6 mg to 10 mg of nonionic surfactants or emulsifiers selected from poloxamers, poloxamer 188 being especially preferred;
70 mg to 90 mg of water soluble diluents selected from mannitol, erythritol, sorbitol, and sucrose; and
0.2 mg to 20 mg of further excipients and/or adjuvants selected from crystalline cellulose, light anhydrous silicic acid, and magnesium stearate.

It should be understood that for capsule formulations it may be of advantage to add a flow control agent such as colloidal silica, light anhydrous silicic acid, or crystalline cellulose before filling the capsule on a capsule filling machine with the powdered pharmaceutical composition in order to improve flow properties of the composition. Therefore, in the capsule formulations the content of the further excipients and/or adjuvants will preferably be in the upper range, e.g., in the range of 10 wt. % to 20 wt. % of the total formulation. In contrast, flow control agents are preferably not added for production of tablet formulations according to the present invention, since these agents, in combination with the high compression forces used in tablet production, deteriorate dissolution or disintegration of the tablets. Therefore, in tablet formulations the content of the further excipients and/or adjuvants will preferably be in the lower range, e.g., in the range of 0.1 wt. % to 5 wt. %, preferably 0.3 wt. % to 2 wt. %, of the final formulation since only low amounts of lubricants should be present.

The tablet formulations according to the present invention can also be used for preparation of fixed dose combination products, for instance, together with a diuretic as the second active component. Suitable diuretics are thiazide and thiazide-analogue diuretics such as hydrochlorothiazide (HCTZ), clopamide, xipamide, or chlorotalidone, and any other diuretic suitable in the treatment of hypertension such as, e.g., furosemide and piretanide, and combinations thereof with amiloride and triamteren. HCTZ is incompatible with basic agents being a component of the telmisartan tablet formulations according to the invention. This problem can be overcome by means of a bilayer pharmaceutical tablet comprising a first telmisartan-containing tablet layer prepared from a pharmaceutical composition mentioned hereinbefore under the first aspect of the invention, and a second tablet layer containing a diuretic in a disintegrating tablet matrix.

The second tablet layer composition generally comprises 1.5 wt. % to 35 wt. %, preferably 2 wt. % to 15 wt. %, of active ingredient; 25 wt. % to 75 wt. %, preferably 35 wt. % to 65 wt. %, of filler; 10 wt. % to 40 wt. %, preferably 15 wt. % to 35 wt. %, of dry binder; 0.5 wt. % to 5 wt. %, preferably 1 wt. % to 4 wt. %, of wet granulation binder; and 1 wt. % to 10 wt. %, preferably 2 wt. % to 8 wt. %, of disintegrant. The other excipients and adjuvants are generally employed in the same amount as in the first tablet layer composition. The filler may be selected from anhydrous lactose, spray-dried lactose, and lactose monohydrate. Tablets of the present invention tend to be very low hygroscopic and may be packaged using PVC-blisters, PVDC-blisters, or a moisture-proof packaging material such as aluminum foil blister packs, polypropylene tubes, glass bottles, and HDPE bottles.

Third Object of the Invention (Process for Preparing Pharmaceutical Compositions and Final Formulations)

The third object of the invention is directed to methods for producing the solid pharmaceutical compositions mentioned hereinbefore. The compositions comprising telmisartan according to the invention may be prepared by any suitable method known to those skilled in the art, for instance, by freeze drying of aqueous solutions, coating of carrier particles in a fluidized bed, and by solvent deposition on sugar pellets or other carriers. Preferably, however, the pharmaceutical compositions are prepared using a granulation process, e.g., the fluid-bed granulation process (A), or, in the alternative, the spray-drying process (B) described specifically hereinafter. The less complicated and cheaper fluid-bed granulation process (A) is preferred.

Since during subsequent processing telmisartan is normally dissolved and transformed into a substantially amorphous form, its initial crystal morphology and particle size are of little importance for the physical and biopharmaceutical properties of the pharmaceutical composition obtained.

In a first embodiment, a fluid-bed granulation process (A) can be used for preparation of the pharmaceutical compositions according to the invention, characterized by the following steps:
(i) preparing a granulation liquid as an aqueous solution by dissolving 3 wt. % to 50 wt. % of telmisartan together with the following components in water or in a mixture solution of ethanol and water:
  (a) a basic agent in a molar ratio of basic agent:telmisartan of 1:1 to 10:|1|, and
  (b) a nonionic surfactant or emulsifier in an amount of about 1 wt. % to 20 wt. %|;
(ii) placing 25 wt. % to 70 wt. % of a water-soluble |diluent| into a fluid-bed granulator, optionally together with 10 wt. % to 20 wt. % of a dry binder, including a premix-step;
(iii) carrying out the fluid-bed granulation using the granulation liquid for spraying onto the components placed into the granulator;
(iv) after completion of the granulation, drying and, optionally, screening the granulate obtained;
(v) optionally blending the granulate with further excipients and/or adjuvants in order to prepare the final composition; and
(vi) optionally milling the granulate thus obtained in order to produce a powdery composition of defined particle size distribution,
wherein all percentage amounts given are related to the final composition to be prepared.

Preferred embodiments of the process with regard to specific components and proportional amounts fully correspond to those disclosed hereinbefore with regard to the first aspect of the invention.

In the premix step of step (ii), an inlet air temperature of about 60° C. to 120° C. may be used. In the granulation step (iii) step, an inlet temperature of about 80° C. to 100° C. may be used. The spraying rate greatly depends on the type of granulator used as well as the batch size and can be adjusted by the skilled person by routine. Only, for instance, a spraying rate of 400 mL/min to 1000 mL/min may be suitable for a 200 kg granulate batch. Lower or higher spray rates may also used.

In the drying step of step (iv), an inlet temperature of about 60° C. to 120° C., and a duration of drying of about 1 minute to 30 minutes may be used. In the screening step, a screen with a mesh size of 0.5 mm to 3 |mm| may be suitable. The optional milling step (vi) can be carried out conventionally by the skilled person.

In a second embodiment, a spray-drying process (B) can be used for preparation of the pharmaceutical compositions according to the invention, characterized by the following steps:

(i) preparing an aqueous spray-solution by dissolving 3 wt. % to 50 wt. % of telmisartan together with the following components in water or mixture solution of ethanol and water:
  (a) a basic agent in a molar ratio of basic agent:telmisartan of 1:1 to 10:|1|, and
  (b) a nonionic surfactant or emulsifier in an amount of about 1 wt. % to 20 wt. %|;
(ii) spray-drying the aqueous spray-solution to obtain a spray-dried granulate;
(iii) mixing the spray-dried granulate with 25 wt. % to 70 wt. % of a water-soluble |diluent| to obtain a premix;
(iv) optionally, mixing the premix with a lubricant; and
(v) optionally, adding further excipients and/or adjuvants in any of steps (i) to (iv),
wherein all percentage amounts given are related to the final composition to be prepared.

If it is necessary to adjust a particular particle size distribution in a powdery composition thus obtained a conventional milling step may be applied, preferably before optional addition of a lubricant according to step (iv). Furthermore, a powdery composition may be converted into a granular composition applying conventional granulation techniques.

Preferred embodiments of the process with regard to specific components and proportional amounts fully correspond to those disclosed hereinbefore with regard to the first aspect of the invention.

In a preferred embodiment of process (B), an aqueous alkaline solution of telmisartan is prepared by dissolving the active ingredient in water or mixture solution of ethanol and water with the help of one or more basic agents like sodium hydroxide or meglumine. Optionally, a recrystallization retarder may be added. The dry matter content of the starting aqueous solution is generally 10 wt. % to 40 wt. %, preferably 20 wt. % to 30 wt. %.

The aqueous solution is then spray-dried at room temperature or preferably at increased temperatures of, for instance, between 50 wt. % and 100° C. in a co-current or countercurrent spray-drier at a spray pressure of, for instance, 1 bar to 4 bar. Generally speaking, the spray-drying conditions are preferably chosen in such a manner that a spray-dried granulate having a residual humidity of ≤5 wt. %, preferably ≤3.5 wt. %, is obtained in the separation cyclone. To that end, the outlet air temperature of the spray-drier is preferably kept at a value of between about 80° C. and 90° C. while the other process parameters such as spray pressure, spraying rate, inlet air temperature, etc. are adjusted accordingly.

The spray-dried granulate obtained is preferably a fine powder having the following particle size distribution:
  $d_{10} \leq 20$ μm, preferably $\leq 10$ μm
  $d_{50} \leq 80$ μm, preferably 20 μm to 55 μm
  $d_{90} \leq 350$ μm, preferably 50 μm to 150 μm After spray-drying, the active ingredient (telmisartan) as well as the excipients contained in the spray-dried granulate, are in a substantially amorphous state with no crystallinity being detectable. From a physical point of view, the spray-dried granulate is a solidified solution or glass having a glass transition temperature ($T_g$) of preferably >50° C., more preferably >80° C.

The lubricant is generally added to the premix in an amount of 0.1 wt. % to 5 wt. %, preferably 0.3 wt. % to 2 wt. %, based on the weight of the final composition.

Mixing is carried out in two stages, i.e., in a first mixing step the spray-dried granulate and the diluent are admixed using, e.g., a high-shear mixer or a free-fall blender, and in a second mixing step the lubricant is blended with the premix, preferably also under conditions of high shear. The method of the invention is, however, not limited to these mixing procedures and, generally, alternative mixing procedures may be employed in any steps of the process comprising a mixing procedure, such as, e.g., container mixing with intermediate screening.

Batches of granulates with different composition obtained by process (A) or (B) may be blended together in order to adjust a target composition and may additionally be blended with further excipients and/or adjuvants such as lubricants, if required for adjusting a final composition for further processing into the final formulation ready for use/ingestion, for instance, for filling into capsules using a suitable capsule filling machine or for direct compression of tablets using a suitable rotary tablet press.

For direct compression, the final composition may be prepared by dry-mixing the constituent components, e.g., by means of a high-intensity mixer or a free-fall blender. Alternatively, the final composition may be prepared using a wet granulation technique wherein an aqueous solution of a wet granulation binder is added to a premix and subsequently the wet granulate obtained is dried, e.g., in a fluidized-bed dryer or drying chamber. The dried mixture is screened and then a lubricant is admixed, e.g., using a tumbling mixer or free-fall blender, whereafter the composition is ready for compression.

A bilayer tablet mentioned under the second aspect of the invention can be prepared by the following process:
(i) providing a first tablet layer composition comprising telmisartan by use of the fluid-bed granulation process (A) or the spray-drying process (B) described hereinbefore,
(ii) providing a second tablet layer composition by:
 (a) mixing and/or granulating a diuretic with the constituents of a disintegrating tablet matrix and, optionally, further excipients and/or adjuvants, and
 (b) admixing a lubricant to obtain a final blend for the second tablet layer;
(iii) introducing the first or the second tablet layer composition in a tablet press;
(iv) compressing said tablet layer composition to form a tablet layer;
(v) introducing the other tablet layer composition into the tablet press; and
(vi) compressing both tablet layer compositions to form a bilayer tablet.

For preparing the bilayer tablet according to the present invention, the first and second tablet layer compositions may be compressed in the usual manner in a bilayer tablet press, e.g., a high-speed rotary press in a bilayer tableting mode. However, care should be taken not to employ an excessive compression force for the first tablet layer. Preferably, the ratio of the compression force applied during compression of the first tablet layer to the compression force applied during compression of both the first and second tablet layers is in the range of from 1:10 to 1:2. For instance, the first tablet layer may be compressed at moderate force of 4 kN to 8 kN, whereas the main compression of first plus second layer is performed at a force of 10 kN to 20 kN.

During bilayer tablet compression, adequate bond formation between the two layers is achieved by virtue of distance attraction forces (intermolecular forces) and mechanical interlocking between the particles.

In order to avoid any cross-contamination between the first and second tablet layers (which could lead to decomposition of HCTZ), any granulate residues have to be carefully removed during tableting by intense suction of the die table within the tableting chamber.

Release Study of the Active Ingredient

The solid oral formulations of the present invention release the active ingredient telmisartan rapidly and with minor pH dependency. Normally, at least 70% and typically at least 80% of the drug load are dissolved after 30 minutes and release of the major fraction occurring within less than 20 minutes.

Table 1 shows a typical capsule formulation containing a pharmaceutical composition according to the invention, designated Formulation |A|, containing as the nonionic surfactant or emulsifier 8 mg of poloxamer 188 (polyoxyethlene[160]polyoxypropylene[30]glycol) and a corresponding reference formulation, designated Formulation |B|, containing instead of the poloxamer component, an additional 8 mg of D-mannitol. The dissolution of these capsule formulations was evaluated in aqueous solutions of pH 1.2 and 4.0 according to JP paddle method, 100 rpm, 900 mL, 37° C., dissolution medium: pH 1.2 JP 1st fluid, pH 4.0 acetic-acid buffer; detection: UV/296 nm.

TABLE 1

Composition of Tested Capsule Formulations

| Ingredient | Formulation A | Formulation B |
|---|---|---|
| telmisartan | 40 mg | 40 mg |
| meglumine | 40 mg | 40 mg |
| poloxamer 188 | 8 mg | 0 mg |
| D-mannitol | 81 mg | 89 mg |
| crystalline cellulose (AVICEL ® PH101) | 30 mg | 30 mg |
| magnesium stearate | 1 mg | 1 mg |
| Total | 200 mg/cap | 200 mg/cap |

The results obtained can be seen in FIGS. 1 and 2 showing release of the active ingredient telmisartan given as "dissolution %". The release of telmisartan was essential faster in the presence of poloxamer 188. FIG. 1 shows the release profile of the active ingredient telmisartan from capsule Formulation A according to the invention in comparison to a corresponding capsule Formulation B without the poloxamer 188 component in aqueous test solution (JP $1^{st}$ fluid) at pH 1.2. FIG. 2 shows the release profile of telmisartan from Formulation A in comparison to Formulation B in aqueous acetic-acid buffer at pH 4.0.

In order to further illustrate the present invention, the following non-limiting examples are given.

The following table shows solid pharmaceutical compositions according to the invention. Formulations C, D, E, F and G are granular formulations which can be filled in capsules, Formulations D, E, F and G also can be compressed to form tablets. All formulations contain 40 mg of telmisartan, whereas alternative capsule and tablet formulations containing 20 mg or 80 mg of telmisartan are homologues formulations.

TABLE 2

| | Formulation | | | | |
|---|---|---|---|---|---|
| Ingredient | C | D | E | F | G |
| telmisartan | 40.0 mg | 40.0 mg | 40.0 mg | 40.0 mg | 40.0 mg |
| meglumine | 40.0 mg | 40.0 mg | 40.0 mg | 40.0 mg | 40.0 mg |
| poloxamer 188 | 8.0 mg | 8.0 mg | 8.0 mg | 8.0 mg | 8.0 mg |
| D-mannitol | 81.5 mg | 80.6 mg | — | 70.6 mg | — |
| erythritol | — | — | 80.5 mg | — | — |

TABLE 2-continued

| Ingredient | Formulation | | | | |
|---|---|---|---|---|---|
| | C | D | E | F | G |
| sorbitol | — | — | — | 10.0 mg | — |
| sucrose | — | — | — | — | 80.6 mg |
| crystalline cellulose | 30.0 mg | — | — | — | — |
| light anhydrous silicic acid | — | — | 0.1 mg | — | — |
| magnesium stearate | 0.5 mg | 1.4 mg | 1.4 mg | 1.4 mg | 1.4 mg |
| Total | 200.0 mg | 170.0 mg | 170.0 mg | 170.0 mg | 170.0 mg |

Manufacturing

1. Granulation Liquid or Spray Solution 90 kg of purified water are measured into a suitable stainless steel vessel at a temperature of between 20° C. to 40° C. In sequence, 8 kg of poloxamer 188 (polyoxyethlene[160]polyoxypropylene[30]glycol), 40 mg of meglumine, and 40 kg of telmisartan (mixture of polymorph A and B) are dissolved in the purified water under intensive stirring until a virtually clear solution is obtained. Total volume is about 160 L.

2. Granulation

Alternative (a) for Producing Formulation C 81.5 kg of D-mannitol and 30 kg of crystalline cellulose (e.g., AVICEL® PH101 or 302) are placed in a fluid-bed granulator, briefly pre-mixed, and sprayed with 178 kg of granulation liquid (containing 88 kg of dry mass). This is then sprayed with 2 L of purified water, followed by a drying step and a screening step.

Alternative (b) for Producing Formulation D 80.6 kg of D-mannitol is placed in a fluid-bed granulator and sprayed with 178 kg of granulation liquid (containing 88 kg of dry mass). This is then sprayed with 2 L of purified water, followed by a drying step and a screening step.

Alternative (c) for Producing Formulation E 80.5 kg of erythritol and 0.1 kg of light anhydrous silicic acid are placed in a fluid-bed granulator and sprayed with 178 kg of granulation liquid (containing 88 kg of dry mass). This is then sprayed with 2 L of purified water, followed by a drying step and a screening step.

Alternative (d) for Producing Formulation F 70.6 kg of erythritol and 10 kg of sorbitol are placed in a fluid-bed granulator and sprayed with 178 kg of granulation liquid (containing 88 kg of dry mass). This is then sprayed with 2 L of purified water, followed by a drying step and a screening step.

Alternative (e) for Producing Formulation G 80.6 kg of sucrose are placed into a fluid-bed granulator and sprayed with 178 kg of granulation liquid (containing 88 kg of dry mass). This is then is sprayed with 2 L of purified water, followed by a drying step and a screening step.

Process Data Pre-Mixing:
Inlet air temperature: 80° C. to 100° C.
End of pre-mixing: gut temperature about 55° C.
Process Data Granulation:
Inlet air temperature: 80° C. to 100° C.
Spraying rate: 500 mL/min to 900 mL/min.
Process Data Drying Step:
Inlet air temperature: 80° C. to 100° C.
End of drying: gut temperature more than 70° C.
Duration of drying: about 5 minutes.

Process Data Screening Step:
The granules are screened, for instance using an oscillator or COMIL® screen machine, with a mesh size of 1.5 mm.

3. Final Mixture for Preparation of Capsule Formulation

Two 199.5 kg batches of screened granules produced according to granulation alternative (a) are mixed using a suitable mixer with a revolution of 10 rpm for 10 minutes to 20 minutes, resulting in a 399 kg mixed batch which is finally blended with 1 kg of magnesium stearate, using a suitable mixer with a revolution of 10 rpm for about 15 minutes, thus producing the final mixture.

4. Final Mixture for Preparation of Tablet Formulation

Two 199.5 kg batches of screened granules produced according to granulation alternative (b), (c), (d), or (e) are mixed using a suitable mixer with a revolution of 10 rpm for 10 minutes to 20 minutes, resulting in a 399 kg mixed batch which is finally blended with 1 kg of magnesium stearate, using a suitable mixer with a revolution of 10 rpm for about 15 minutes, thus producing the final mixture.

5. Capsule Filling

The final mixture for capsule formulation is filled into capsules using a suitable capsule filling machine (100 mg, 200 mg, or 400 mg per capsule).

6. Tablet Compression

Using a suitable rotary tablet press, the final mixture for tablet compression is compressed into tablets. The target weight is 85 mg, 170 mg, or 340 |mg|.

| Process Parameters for Tabletting | |
|---|---|
| Tablet press | FETTE ® 3090 |
| Tabletting speed | 100,000 (80,000 to 120,000) tabl./h |
| Stirrer blade speed | about 30 rpm |
| Compression force | 7 (5 to 10) kN |

The tablet hardness can be adjusted by variation of the main compression force.

8. Production of a Spray-Dried Formulation

The spray-solution described above is sprayed into a suitable spray dryer, e.g., a NIRO™ 6.3 equipped with SCHLICK™ atomizing nozzles of 1.0 mm diameter, with a flow-through heating coil connected upstream of the dryer, and dried to give a white to off-white fine granulate. The spray mode is countercurrent at a spray-pressure of about 3 bar, an inlet air temperature of about 125° C., and a spray rate of about 11 kg/h, thus resulting in an outlet air temperature of about 85° C. The temperature of the flow through heating coil water bath is set at a temperature of about 80° C.

88 kg of the spray-dried granules are mixed with 80.6 kg of powdered D-mannitol using a suitable mixer with a revolution of 10 rpm for about 15 minutes and finally blended with 1.4 kg of magnesium stearate, thus producing the final mixture ready for filling into capsules or compression into tablets.

We claim:

1. A solid pharmaceutical composition capsule or tablet comprising 3 wt. % to 50 wt. % telmisartan dispersed in a dissolving matrix comprising:
(a) a basic agent, selected from NaOH, KOH, NaHCO$_3$, KHCO$_3$, Na$_2$CO$_3$, K$_2$CO$_3$, Na$_2$HPO$_4$, K$_2$HPO$_4$ or meglumine, in a molar ratio of basic agent:telmisartan of 1:1 to 10:1;
(b) about 1 wt. % to about 20 wt. % of polyoxamers having an average molecular weight of about 2000 to 12000;
(c) 25 wt. % to 70 wt. % of a water-soluble diluent; and
(d) 0 wt. % to 20 wt. % of one or more additional excipients and/or adjuvants,
wherein the sum of all components is 100%; and wherein the pharmaceutical composition is a solid in the form of a capsule or a tablet.

2. The pharmaceutical composition of claim 1, wherein the poloxamers comprise poloxamer 182LF, poloxamer 331, or poloxamer 188.

3. The pharmaceutical composition of claim 1, wherein the water-soluble diluent is selected from carbohydrates, oligosaccharides, and sugar alcohols.

4. The pharmaceutical composition of claim 1, wherein the water-soluble diluent is glucose, sucrose, erythritol, sorbitol, mannitol, dulcitol, ribitol, or xylitol.

5. The pharmaceutical composition of claim 1, wherein the additional excipients and/or adjuvants are selected from binders, carriers, lubricants, flow control agents, crystallization retarders, solubilizers, and coloring agents.

6. The pharmaceutical composition of claim 1, comprising a dosage unit of 10 mg to 160 mg of telmisartan.

7. The pharmaceutical composition of claim 1, comprising a dosage unit of 10 mg to 160 mg of telmisartan.

8. A bilayer pharmaceutical tablet comprising:
   (a) a first telmisartan-containing tablet layer comprising the pharmaceutical composition of one of claims 1 or 2 to 5; and
   (b) a second tablet layer containing a diuretic in a disintegrating tablet matrix.

9. A process for preparing the pharmaceutical composition of claim 1 using a fluid-bed granulation process, comprising:
   (i) preparing a granulation liquid as an aqueous solution by dissolving 3 wt. % to 50 wt. % of telmisartan together with the following components in water or in a mixture solution of ethanol and water:
      (a) a basic agent, selected from NaOH, KOH, $NaHCO_3$, $KHCO_3$, $Na_2CO_3$, $K_2CO_3$, $Na_2HPO_4$, $K_2HPO_4$ or meglumine, in a molar ratio of basic agent:telmisartan of 1:1 to 10:1, and
      (b) polyoxamers having an average molecular weight of about 2000 to 12000 in an amount of about 1 wt. % to about 20 wt. %;
   (ii) placing 25 wt. % to 70 wt. % of a water-soluble diluent in a fluid-bed granulator, optionally together with 10 wt. % to 20 wt. % of a dry binder, including a premix-step;
   (iii) carrying out the fluid-bed granulation using the granulation liquid for spraying on the components placed in the granulator;
   (iv) drying the granulation thus obtained and, optionally, screening the granulate obtained;
   (v) optionally blending the granulate with one or more additional excipients and/or adjuvants;
   (vi) optionally milling the granulate thus obtained in order to produce a powdery composition of defined particle size distribution; and
   (vii) providing the granulate in a tablet or capsule form;
wherein all percentage amounts given are related to the final composition to be prepared.

10. A process for preparing the pharmaceutical composition of claim 1 using a spray drying process, comprising:
   (i) preparing an aqueous spray-solution by dissolving 3 wt. % to 50 wt. % of telmisartan together with the following components in water or mixture solution of ethanol and water:
      (a) a basic agent, selected from NaOH, KOH, $NaHCO_3$, $KHCO_3$, $Na_2CO_3$, $K_2CO_3$, $Na_2HPO_4$, $K_2HPO_4$ or meglumine, in a molar ratio of basic agent:telmisartan of 1:1 to 10:1, and
      (b) polyoxamers having an average molecular weight of about 2000 to 12000 in an amount of about 1 wt. % to 20 wt. %;
   (ii) spray-drying the aqueous spray-solution to obtain a spray-dried granulate;
   (iii) mixing the spray-dried granulate with 25 wt. % to 70 wt. % of a water-soluble diluent to obtain a premix;
   (iv) optionally mixing the premix with a lubricant;
   (v) optionally adding additional excipients and/or adjuvants in any of steps (i) to (iv); and
   (vi) providing the granulate in a tablet or capsule form;
wherein all percentage amounts given are related to the final composition to be prepared.

* * * * *